United States Patent [19]
Galaj et al.

[11] Patent Number: 5,847,171
[45] Date of Patent: Dec. 8, 1998

[54] MOLECULAR ORGANIC COMPOUND WITH FERROMAGNETIC PROPERTIES AND A METHOD OF PRODUCING IT

[75] Inventors: Stanislas Galaj, Arcueil; Alain Le Mehaute, Gif Sur Yvette, both of France

[73] Assignee: Alcatel Alsthom Compagnie Generale D'Electricite, Paris Cedex, France

[21] Appl. No.: 892,521

[22] Filed: Sep. 16, 1997

Related U.S. Application Data

[62] Division of Ser. No. 631,230, Apr. 12, 1996, Pat. No. 5,714,622.

[30] Foreign Application Priority Data

Apr. 14, 1995 [FR] France .................................. 95 04530

[51] Int. Cl.[6] .......................... C07C 50/06; C07C 50/08
[52] U.S. Cl. ........................ 552/301; 552/305; 552/307; 552/308; 552/294; 552/295
[58] Field of Search ..................... 552/301, 305, 552/307, 308, 294, 295

[56] References Cited

U.S. PATENT DOCUMENTS

| | | | |
|---|---|---|---|
| 3,963,498 | 6/1976 | Trevoy et al. | 96/87 |
| 5,408,034 | 4/1995 | Galaj et al. | 528/422 |

FOREIGN PATENT DOCUMENTS

| | | |
|---|---|---|
| 0545819A1 | 6/1993 | European Pat. Off. . |
| 0645414A1 | 3/1995 | European Pat. Off. . |
| 2125602 | 9/1972 | France . |
| A-4-320883 | 11/1992 | Japan . |
| A-7-43918 | 2/1995 | Japan . |

*Primary Examiner*—Allen J. Robinson
*Assistant Examiner*—Barbara Badio
*Attorney, Agent, or Firm*—Sughrue, Mion, Zinn, Macpeak & Seas, PLLC

[57] ABSTRACT

The invention is drawn to organic compounds of the general formulae L—A—Z or L—A'—L' as defined in the specification. The compounds are readily crystallizable and can be used for their ferromagnetic properties.

12 Claims, 1 Drawing Sheet

MOLECULAR ORGANIC COMPOUND WITH FERROMAGNETIC PROPERTIES AND A METHOD OF PRODUCING IT

This is a divisional of application Ser. No. 08/631,230 filed Apr. 12, 1996, now U.S. Pat. No. 5,714,622.

The present invention relates to a family of readily crystallizable molecular organic compounds with ferromagnetic properties.

BACKGROUND OF THE INVENTION

An organic copolymer with ferromagnetic properties has been suggested in which the elementary unit comprises a first group of amino-aromatic compounds derived from 1-naphthylamine and corresponding iminoquinone forms, attached to a second group of substituted aminoaromatic compounds. The second group is selected from substituted amine compounds containing at least one aniline unit in its structure, the compounds derived from aniline having a substituent which is connected to the nucleus by an ethynylene or paraphenylene chain, and corresponding iminoquinone compounds. That copolymer is weakly ferromagnetic and difficult to crystallize.

Crystalline inclusion compounds of metal salts in that copolymer are known, but those are only obtained in relatively low yields.

OBJECTS AND SUMMARY OF THE INVENTION

The aim of the present invention is to provide a molecular organic compound with stronger magnetization than that of known copolymers.

A further aim of the invention is to provide a compound whose production, in particular crystallization, is easy to carry out and provides improved yields.

The present invention provides an organic compound with ferromagnetic properties, which is a molecular compound with one of the following general formulae:

   (I)

   (II)

where:
—A— is selected from a radical from a benzene nucleus which is multivalent in the para position and which may be substituted, and a radical from a naphthalene nucleus which is multivalent in the position para to one of the nuclei and which may be substituted;

—Z— is a mono— or bivalent radical selected from hydrogen, a nitrile radical, a nitro radical, a fluoro radical, a chloro radical, a bromo radical, an iodo radical, an amino radical, an imino radical, an alkylamino radical, a dialkylamino radical, a dialkylimino radical, a trialkylammonio radical, an aminocyclic radical in which one carbon atom in the ring can be replaced by a heteroatom such as O, S or N, a sulfo radical, a carboxy radical, a phosphono radical, an arsono radical, an acyl radical, a formamido radical, an acetamido radical and an acetimido radical;

—A'— is selected from a radical from a benzene nucleus which is multivalent in the para or ortho position and which may be substituted;

—L and —L' have the form:

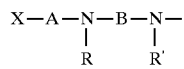

where N is a nitrogen atom; where:
—X is a mono- or bivalent radical which can fix a proton, selected from a first group of compounds constituted by an amino radical, an imino radical, an alkylamino radical, a dialkylamino radical, a dialkylimino radical, a trialkylammonio radical and an aminocyclic radical in which one carbon atom in the ring can be replaced by a heteroatom such as O, S or N, and a second group of compounds constituted by a sulfo radical, a carboxy radical, a phosphono radical and an arsono radical;

—NR— and —NR'— are multivalent radicals from a primary amine or ammonia;

—B— is selected from a radical from a naphthalene nucleus which is multivalent in the position para to one of the nuclei and has at least one substituent Y in the 6 or 7 position on the other nucleus, a radical from a multivalent benzene nucleus which has at least one substituent Y in the 2 or 3 position bonded to the nucleus via an ethynylene link or a paraphenylene link which may be substituted, said substituent Y being selected from a sulfo radical, a carboxy radical, a phosphono radical, and an arsono radical when —X is selected from the first group of compounds, and said substituent Y being selected from an amino radical, an imino radical, an alkylamino radical, a dialkylamino radical, a dialkylimino radical, a trialkylammonio radical, and an aminocyclic radical in which one carbon atom in the ring can be replaced by a heteroatom such as O, S or N when —X is selected from said second group of compounds.

The organic molecular compound of the present invention can be described as a linear chain of multivalent radicals. The nature of the bonds forming the chain depends on whether the radicals are in the reduced or oxidized state. In the reduced form, —A—, —A'—, —B—, —NR— and —NR'— are bivalent, and —X, —Y and —Z are monovalent. In the oxidized form, —A—, —A'— and —B— are tetravalent, —NR— and —NR'— are trivalent, and —X, —Y and —Z are bivalent.

The compound of the invention in its reduced form does not exhibit ferromagnetism; in its oxidized form, ferromagnetic properties are clearly observable. Radicals —L and —L' are the base units at the origin of the ferromagnetism. Because of the structure of radical —B—, an interaction between substituent Y which it carries and radicals —NR— and —NR'— which are bonded to it is impossible. In contrast, an acid-base interaction can occur between acid substituent Y and one of the radicals —NR— and —NR'— located at the opposite side to the closest units —A— or —A'—, allowing the occurrence of ferromagnetism. When radicals —X and —Z are basic, while Y is an acid site, or when radicals —X and —Z are acid while Y is a basic site, the interaction can also lead to the formation of an internal salt and contribute to the ferromagnetism of the molecular compound.

Due to steric hindrance, radicals —A—Z and —A'— orientate the stereochemistry of the chain during synthesis and block rotation about the B—N bonds in the molecular compound.

In a first embodiment of the present invention, —A— is a radical from a benzene nucleus which is multivalent in the para position having one to four substituents $R_a$ independently selected from hydrogen, an alkyl radical, a cycloalkyl radical, an alkoxy radical, an alkoxyalkyl radical, a nitrile radical, a nitro radical and a hydroxyalkyl radical, with the following form:

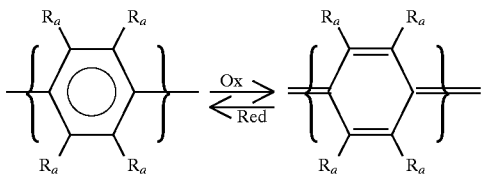

In a second embodiment, —A— is a multivalent radical from a naphthalene nucleus having one to four substituents $R_b$ in the 5, 6, 7 and/or 8 positions, independently selected from hydrogen, an alkyl radical, a cycloalkyl radical, an alkoxy radical, an alkoxyalkyl radical, a nitrile radical, a nitro radical, a hydroxyalkyl radical, a fluoro radical, a chloro radical, a bromo radical and an iodo radical, and having one or two substituents $R_c$ in the 2 and/or 3 position independently selected from hydrogen, an alkyl radical, a cycloalkyl radical, an alkoxy radical, and an alkoxyalkyl radical, with the following form:

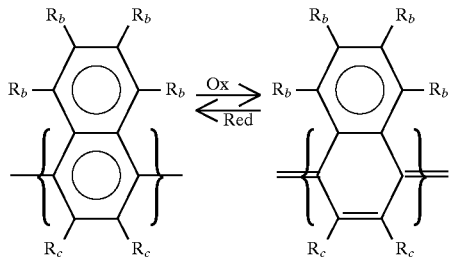

In a third embodiment, —A— is a multivalent radical from a tetrahydronaphthalene nucleus having one to four substituents $R_d$ in the 5, 6, 7 and/or 8 positions independently selected from hydrogen, an alkyl radical, a cycloalkyl radical, an alkoxy radical, an alkoxyalkyl radical, a hydroxyalkyl radical, a fluoro radical, a chloro radical, a bromo radical and an iodo radical, and having one or two substituents $R_e$ in the 2 and/or 3 position selected from hydrogen, an alkyl radical, a cycloalkyl radical, an alkoxy radical, and an alkoxyalkyl radical, with the following form:

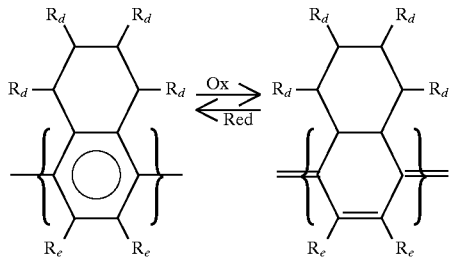

In a fourth embodiment, —A'— is a radical from a benzene nucleus which is multivalent in the para position having one to four substituents independently selected from hydrogen, an alkyl radical, a cycloalkyl radical, an alkoxy radical, an alkoxyalkyl radical, a nitrile radical, a nitro radical and a hydroxyalkyl radical.

In a fifth embodiment, —A'— is a radical from a benzene nucleus which is multivalent in the ortho position having one to four substituents $R_f$ independently selected from a hydrogen, an alkyl radical, a cycloalkyl radical, an alkoxy radical, an alkoxyalkyl radical and a hydroxyalkyl radical.

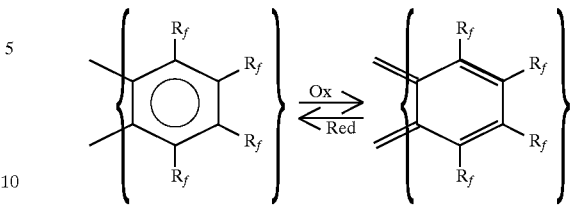

In a sixth embodiment, —B— is a multivalent radical from a naphthalene nucleus having one or two substituents $R_g$ in the 2 and/or 3 position on the multivalent nucleus, independently selected from hydrogen, a nitrile radical, a nitro radical, a fluoro radical, a chloro radical, a bromo radical and an iodo radical, and having said substituent Y on the other nucleus in the 6 or 7 position, and one to three substituents $R_h$ in the 5, 8 and/or in the available 6 or 7 position, independently selected from hydrogen, an alkyl radical, a cycloalkyl radical, an alkoxy radical, an alkoxyalkyl radical, a nitrile radical, a nitro radical and a hydroxyalkyl radical, a fluoro radical, a chloro radical, a bromo radical and an iodo radical, with the following form:

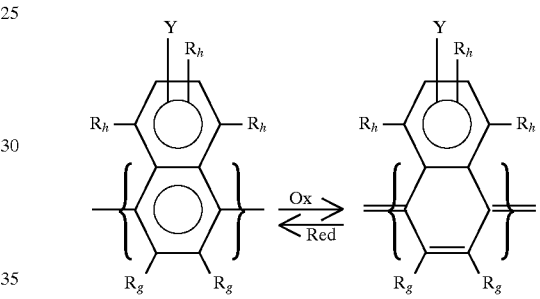

In a seventh embodiment, —B— is a multivalent radical from a benzene nucleus having said substituent Y bonded to the nucleus via a paraphenylene link in the 2 or 3 position, said link having said substituent Y in the 4 position and one or two substituents $R_i$ in the 2 and/or 6 position, independently selected from hydrogen, an alkyl radical, a cycloalkyl radical, an alkoxy radical, an alkoxyalkyl radical and a hydroxyalkyl radical, with the following form:

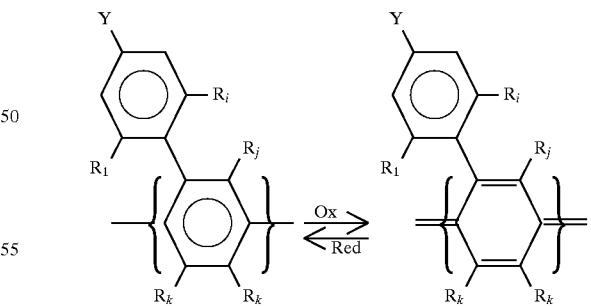

In this case, radical —B— can be considered to be a derivative of biphenyl. The paraphenylene link constitutes a rigid arm connecting the multivalent radical via carbon number 1 to substituent Y in the para position via carbon number 4. Positions 2 and 6 are free to receive one or two substituents $R_j$.

In an eighth embodiment, —B— is a multivalent radical from a benzene nucleus having said first substituent Y bonded to the nucleus via an ethynylene link or via a paraphenylene link which may be substituted, said link being in the 2 or 3 position, a second substituent $R_j$ being in the other 2 or 3 position, independently selected from hydrogen, an alkyl radical, a cycloalkyl radical, an alkoxy radical, an alkoxyalkyl radical, a hydroxyalkyl radical, a fluoro radical, a chloro radical, a bromo radical and an iodo radical, and a third and/or fourth substituent $R_k$ in the 5 and/or 6 position, independently selected from hydrogen, a fluoro radical, a chloro radical, a bromo radical and an iodo radical.

When radical —B— contains an ethynylene link, it can be considered to be a derivative of phenylacetylene. It has the following form:

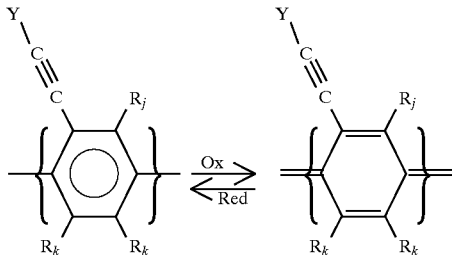

In a ninth embodiment, —R and —R' are independently selected from hydrogen, an alkyl radical, a cycloalkyl radical and a hydroxyalkyl radical. In the reduced state, radicals —NR— and —NR'— are bivalent and bond a reduced —A— radical to a reduced —B— radical; in the oxidized state, these radicals are trivalent and bond an oxidized —A— radical to a reduced —B— radical or a reduced —A— radical to an oxidized —B— radical.

A further object of the present invention is constituted by a method of producing the compound of the invention, comprising forming a chain of at least one aminoaromatic compound, which may be substituted, with an aminosulfonic acid containing two condensed benzene nuclei, said chain being formed in an alcoholic solution, in the presence of a weak acid and an oxidizing agent.

Preferably, the oxidizing agent is selected from hydrogen peroxide and ammonium peroxodisulfate.

Preferably, said aminosulfonic acid containing two condensed benzene nuclei is selected from Cleve's acids such as 5-amino-2-naphthalenesulfonic acid (β form) and 8-amino-2-naphthalenesulfonic acid (θ form).

Preferably, said aminoaromatic compound is selected from a paraphenylenediamine, an N,N-dialkyl-paraphenylenediamine and an N,N-dialkylaniline.

In a variation, the method further comprises reduction by a strong reducing agent and forming a chain with a substituted aminoaromatic compound.

In a first implementation of the method of the invention, said substituted aromatic compound has a first halogen substituent and a second substituent selected from a cyano substituent in the position para to the halogen, a nitro substituent in the position para to the halogen, and two nitro substituents in positions ortho and para to the halogen.

In a second implementation of the method of the invention, said substituted aromatic compound is an arylamine which is dialkylated on the nitrogen atom.

Preferably, said strong reducing agent is hydrazine in the presence of Raney nickel.

In a further variation, the method further comprises a purification step, and optionally a crystallization step, for the compound of the invention.

In a still further variation, the method also comprises an oxidation step for said compound of the invention, in which oxidation is carried out using a peroxodisulfate in aqueous solution. The condensation products, in the reduced state, do not exhibit ferro-magnetism at ambient temperature. A ferromagnetic compound is obtained by oxidizing the compound. This is preferably carried out using a peroxodisulfate in aqueous solution.

The compound of the invention is thus synthesized from sub-assemblies comprising a number of radicals which are already bonded together.

While molecular compounds comprising more than two —L radicals can be produced using an analogous method, they are of limited importance. On the one hand, the number of method steps required to produce them rapidly increases, and on the other hand the reaction yield falls off to a great extent due to the formation of secondary, non-ferromagnetic, species.

BRIEF DESCRIPTION OF THE DRAWING

Further characteristics and advantages of the present invention will become clear from the following examples, which are given by way of illustration only and are in no way limiting and are made with reference to the accompanying drawing.

In the accompanying drawing.

MORE DETAILED DESCRIPTION

Figure 1:
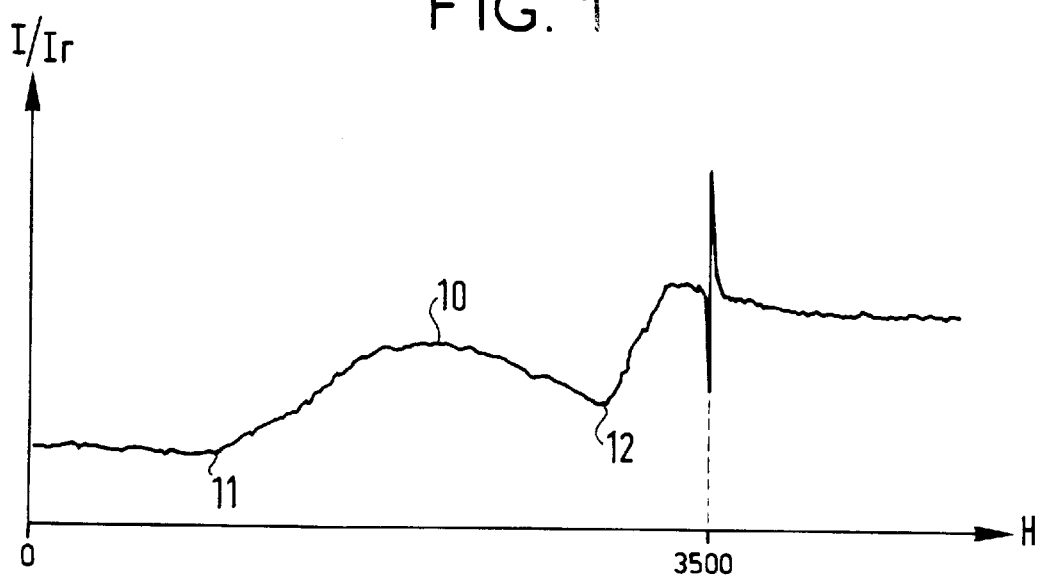
FIG. 1 shows the ferromagnetic resonance spectrum of the compound of the present invention in its partially oxidized state.
Figure 2:
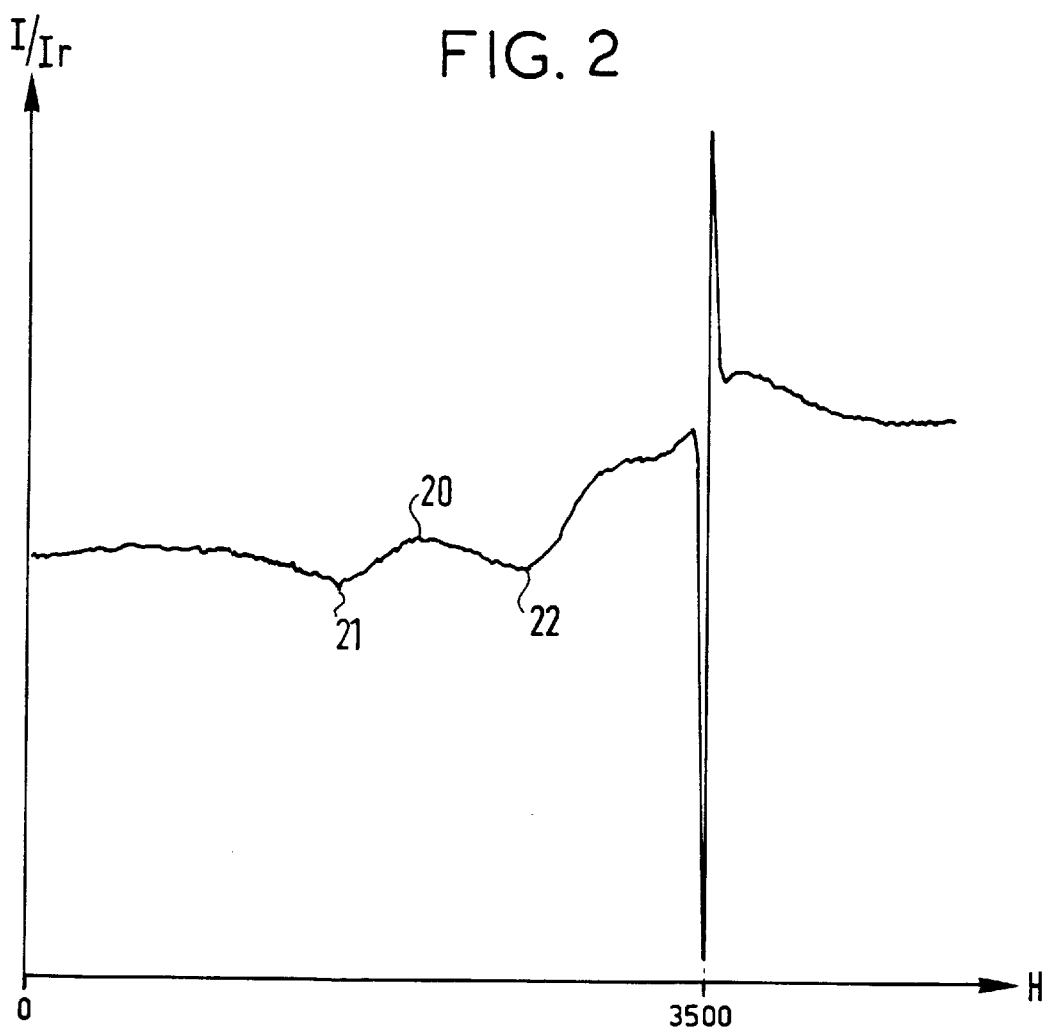
FIG. 2 shows the ferromagnetic resonance spectrum of the compound of the invention after oxidation.

In FIGS. 1 and 2, the magnetic field H in units of $10^{-4}$ Tesla (1 Gauss) is along the abscissa, and the ordinate shows the ratio $I/I_r$ between the absorption of the compound and the absorption of the reference, in arbitrary relative units.

EXAMPLE 1

1.36 grams (g) of N,N-dimethyl-paraphenylenediamne ($10^{-2}$ mole) and 2.23 g of finely powdered 5-amino-2-naphthalenesulfonic acid (βform of Cleve's acid) were introduced into an Erlenmeyer flask containing 40 milliliters (ml) of ethanol and 5 ml of acetic acid. 1.2 ml of a 50% by weight solution of hydrogen peroxide ($2 \times 10^{-2}$ mole) was added. The mixture was stirred at ambient temperature for 30 minutes (min) then the suspension was filtered. The filtrate was poured into 200 ml of water. A blue-green precipitate appeared which was recovered by centrifuging. The product was washed with N-propanol then dried.

This product did not exhibit ferromagnetism at ambient temperature or at 119 K. It was obtained in accordance with the reaction:

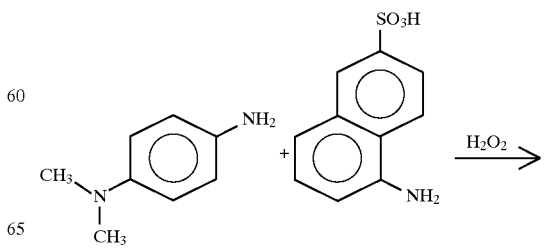

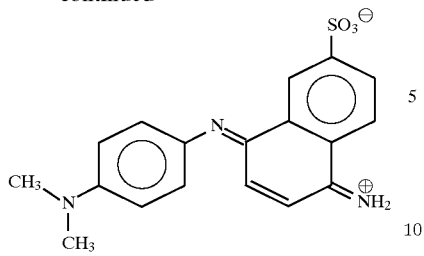

The product obtained above was dispersed in 30 ml of ethanol containing 1 g of Raney nickel and 5 ml of anhydrous hydrazine and slowly brought to boiling point over 30 min then refluxed for 15 min at that temperature. The Raney nickel was completely removed using a magnet. After filtering and evaporating off the solvent, a reduced product was recovered which did not exhibit ferromagnetism at ambient temperature, which had the following formula:

The residue was refluxed at 140° C. or 4 hours in 20 ml of N-butanol in the presence of 2 g of 1-chloro-2,4-dinitrobenzene. The compound was obtained in accordance with the following reaction:

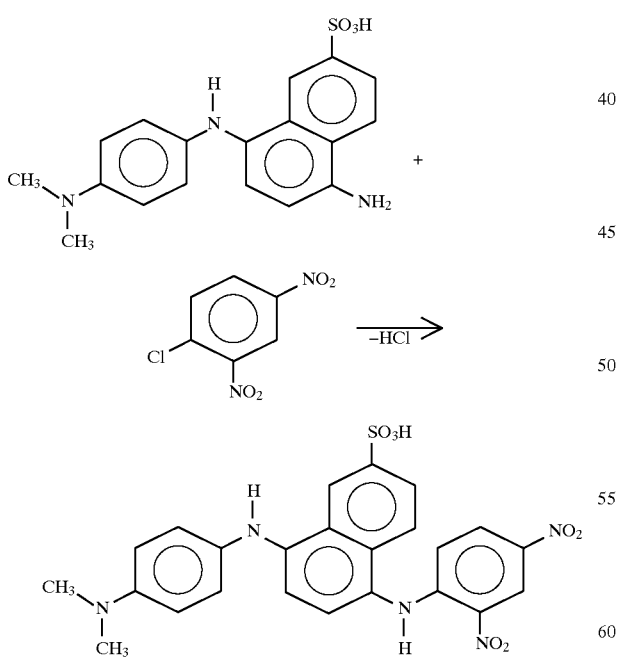

The suspension in N-butanol was cooled then diluted in 50 ml of acetone. This was all poured into 300 ml of water containing 2.25 g of ammonium peroxodisulfate. After 30 min of oxidation at ambient temperature with stirring, the precipitate was recovered by centrifuging, washed with water, then with acetone and with ethyl ether, and finally dried. 226 milligrams (mg) of a dark blue powder with ferromagnetic properties was obtained in a yield of 4%. The oxidized compound had an iminoquinone structure which was between the following end forms:

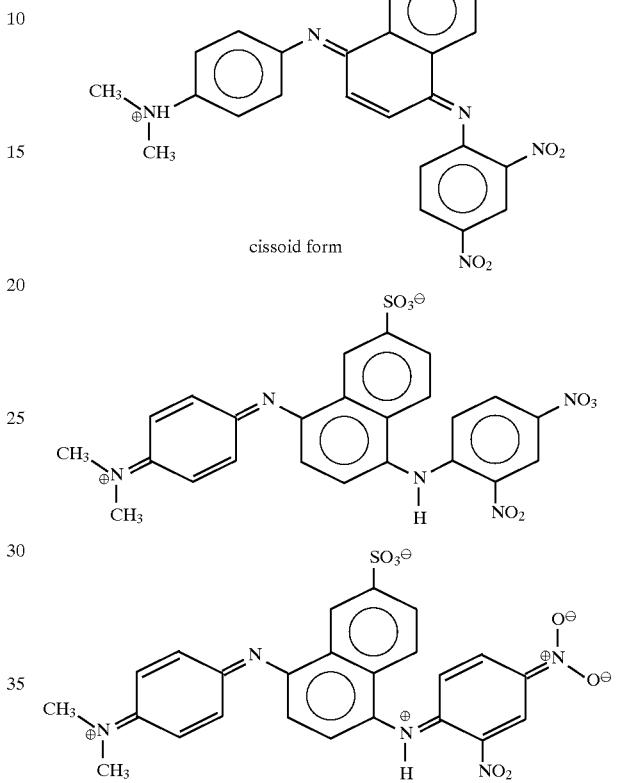

The cissoid form of the compound, after washing and drying, rearranged by formation of an internal salt between XA— and —BY—, resulting in creation of a biradical with a triplet state and aromatization of the substituted radical —BY—. The compound of the invention thus had the following form:

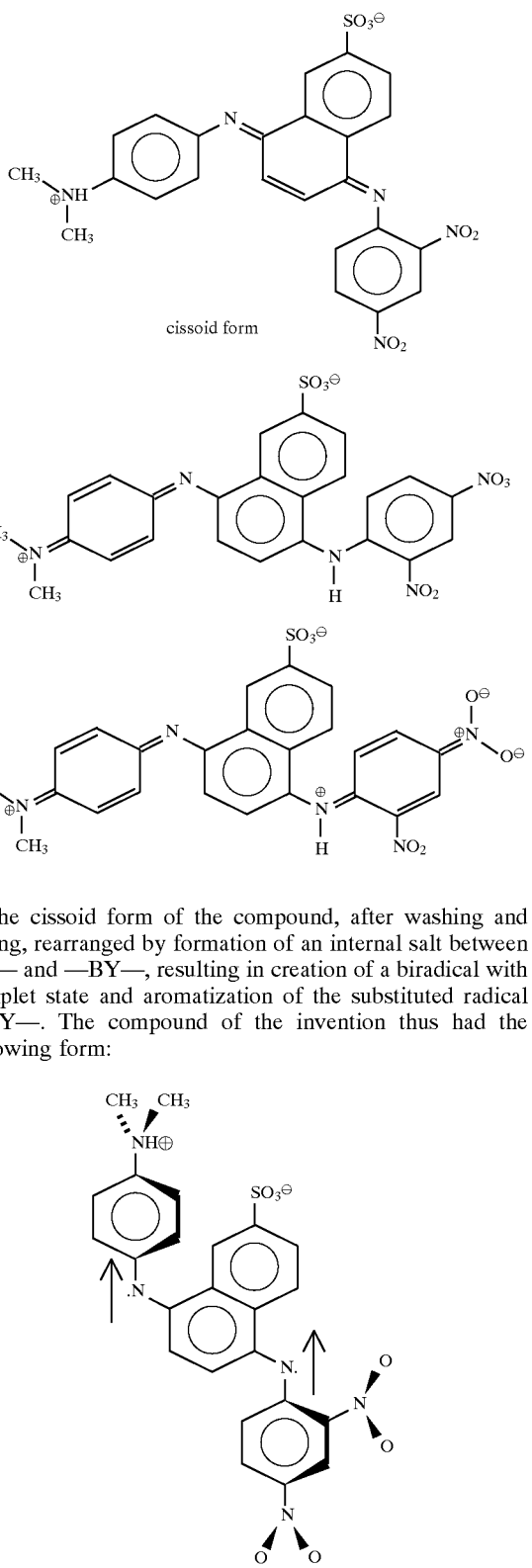

Ferromagnetic resonance spectra were recorded at ambient temperature at a frequency of 9.43 Gigahertz (GHz). The curves obtained were derivatives of the resonance curves.

The compound of the invention, in its partially oxidized state by dint of a period of 30 min in an aqueous solution of ammonium peroxododisulfate, had two ferromagnetic resonance bands which can be seen in the ferromagnetic resonance spectrum of FIG. 1 (curve 10): a first peak 11 corresponded to a field of $3130 \times 10^{-4}$ (3130 Gauss) and a second peak 12 corresponded to a field of $1560 \times 10^{-4}$ Tesla (1560 Gauss).

After prolonged oxidation by dint of a period of 48 hours in the same solution which was three times more concentrated, the compound of the invention had a more complex resonance spectrum. In FIG. 2 (curve 20), a first band 21 corresponding to a field of $3450 \times 10^{-4}$ Tesla (3450 Gauss), a second band 22 corresponding to a field of $2680 \times 10^{-4}$ Tesla (2680 Gauss) and a third band corresponding to a field of $1820 \times 10^{-4}$ Tesla (1820 Gauss) can be seen. Since the oxidation reaction was fairly slow, the gradual increase in ferromagnetism could be observed as it developed.

EXAMPLE 2

1.21 g of N,N-dimethylaniline ($10^{-2}$ mole) and 1.36 g of N,N-dimethyl-paraphenylenediamine ($10^{-2}$ mole) were dissolved in a beaker containing 25 ml of acetic acid. A solution constituted by 2.23 g of βCleve's acid ($10^{-2}$ mole), 2 ml of ammonia (d=0.89) and 25 ml of water were added to the beaker. 1.75 ml of a 50% by weight solution of hydrogen peroxide ($3 \times 10^{-2}$ mole) was then introduced. The reaction was carried out at ambient temperature for one hour, with stirring. Filtering eliminated the unreacted Cleve's acid. The filtrate was diluted in 200 ml of water and the pH of the suspension was brought to 7 by addition of concentrated ammonia. The suspension was centrifuged, then the concentrate was washed by successive redispersion operations in a solvent and centrifuging. The operation was carried out three times using water, three times using ethanol and finally three times using diethyloxide.

After drying, a blue-green powder containing the following semi-oxidized product was obtained in a yield of 30%, mixed with other, secondary, products:

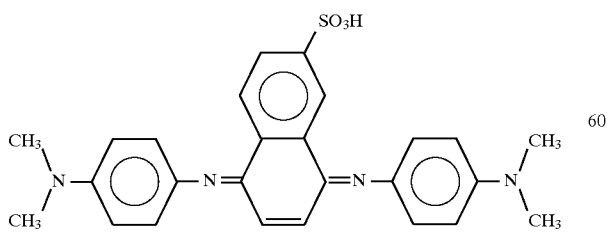

This powder had a magnetization of the order of 0.05 emu/g.

EXAMPLE 3

2.42 g of N,N-dimethylaniline ($2 \times 10^{-2}$ mole) and 1.08 g of paraphenylenediamine ($10^{-2}$ mole) were dissolved in a beaker containing 25 ml of acetic acid. A solution constituted by 4.46 g of θCleve's acid ($2 \times 10^{-2}$ mole), 4 ml of ammonia (d=0.89) and 50 ml of water were added to the beaker. 13.7 g of ammonium peroxodisulfate was added in tiny amounts over one hour. The reaction was carried out at ambient temperature, with stirring.

The method described in Example 2 for filtering and centrifuging was followed.

After drying, a blue-green powder containing the following semi-oxidized product was obtained, in a yield of 20%, mixed with other, secondary, products:

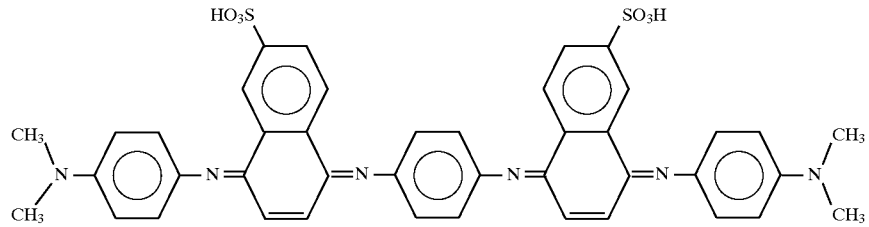

This powder had a magnetization of the order of 0.03 emu/g.

The present invention is not limited to the described embodiments, but can be varied by the skilled person without departing from the spirit of the invention.

We claim:

1. A method of producing an organic compound with ferromagnetic properties, comprising a molecular compound with one of the following general formulae:

$$L—A—Z \quad (I)$$

$$L—A'—L' \quad (II)$$

where:
- —A— is selected from a radical from a benzene nucleus which is multivalent in the para position and which is optionally substituted, and a radical from a naphthalene nucleus which is multivalent in the position para to one of the nuclei and which is optionally substituted;
- —Z— is a mono- or bivalent radical selected from hydrogen, a nitrile radical, a nitro radical, a fluoro radical, a chloro radical, a bromo radical, an iodo radical, an amino radical, an imino radical, an alkylamino radical, a dialkylamino radical, a dialkylimino radical, a trialkylammonio radical, an aminocyclic radical in which one carbon atom in the ring is optionally substituted by a heteroatom, a sulfo radical, a carboxy radical, a phosphono radical, an arsono radical, an acyl radical, a formamido radical, an acetamido radical and an acetimido radical;

—A'— is selected from a radical from a benzene nucleus which is multivalent in the para or ortho position and which is optionally substituted;

—L and —L' have the form:

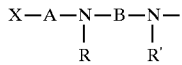

where N is a nitrogen atom; where:

—X is a mono- or bivalent radical which can fix a proton, selected from a first group consisting of an amino radical, an imino radical, an alkylamino radical, a dialkylamino radical, a dialkylimino radical, a trialkylammonio radical and an aminocyclic radical in which one carbon atom in the ring is optionally substituted by a heteroatom, or selected from a second group consisting of a sulfo radical, a carboxy radical, a phosphono radical and an arsono radical;

—NR— and —NR'— are multivalent radicals from a primary amine or ammonia where N is a nitrogen atom;

—B— is selected from a radical from a naphthalene nucleus in which one of the nuclei is bonded to nitrogen atoms positioned para to each other and in which the other nucleus has at least one substituent Y in the 6 or 7 position, a radical from a multivalent benzene nucleus which has at least one substituent Y in the 2 or 3 position bonded to the nucleus via an ethenylene link or a paraphenylene link which is optionally substituted, said substituent Y being selected from a sulfo radical, a carboxy radical, a phosphono radical, and an arsono radical when —X is selected from the first group of compounds, and said substituent Y being selected from an amino radical, an imino radical, an alkylamino radical, a dialkylamino radical, a dialkylimino radical, a trialkylammonio radical and an aminocyclic radical in which one carbon atom in the ring is optionally substituted by a heteroatom when —X is selected from said second group of compounds, said organic compound being in its reduced form or in its oxidized form, said method comprising forming a chain of at least one aminoaromatic compound, which is optionally substituted, with an aminosulfonic acid containing two condensed benzene nuclei, said chain being formed in an alcoholic solution, in the presence of a weak acid and an oxidizing agent.

2. A method according to claim 1, in which said oxidizing agent is selected from hydrogen peroxide and ammonium peroxodisulfate.

3. A method according to claim 1, in which said aminosulfonic acid containing two condensed benzene nuclei is selected from 8-amino-2-naphthalenesulfonic acid and 5-amino-2-naphthalenesulfonic acid.

4. A method according to claim 1, in which said aminoaromatic compound is selected from a paraphenylenediamine, an N,N-dialkylparaphenylenediamine and an N,N-dialkylaniline.

5. A method according to claim 1, further comprising reduction by a strong reducing agent and condensation with a substituted aminoaromatic compound.

6. A method according to claim 5, in which said substituted aromatic compound has a first halogen substitutent and a second substituent selected from a cyano substituent in the position para to the halogen, a nitro substituent in the position para to the halogen, and two nitro substitutents in positions ortho and para to the halogen.

7. A method according to claim 5, in which said substituted aromatic compound is an arylamine which is dialkylated on the nitrogen atom.

8. A method according to claim 5, in which said strong reducing agent is hydrazine in the presence of Raney nickel.

9. A production method according to claim 1, further comprising a purification step for said compound.

10. A production method according to claim 9, further comprising a crystallization step for said compound.

11. A production method according to claim 1, further comprising an oxidation step for said compound.

12. A production method according to claim 11, in which said oxidation is carried out using a peroxodisulfate in aqueous solution.

* * * * *